(12) United States Patent
Deno et al.

(10) Patent No.: US 7,184,832 B2
(45) Date of Patent: Feb. 27, 2007

(54) REFRACTORY PERIOD TRACKING AND ARRHYTHMIA DETECTION

(75) Inventors: D. Curtis Deno, Andover, MN (US); Ruth N. Klepfer, St. Louis Park, MN (US); William J. Havel, Maple Grove, MN (US); David M. Schneider, New Haven, CT (US); Vincent E. Splett, Apple Valley, MN (US)

(73) Assignee: Medtronic, Inc., Minneapolis, MN (US)

( * ) Notice: Subject to any disclaimer, the term of this patent is extended or adjusted under 35 U.S.C. 154(b) by 470 days.

(21) Appl. No.: 10/680,528

(22) Filed: Oct. 7, 2003

(65) Prior Publication Data

US 2005/0075676 A1    Apr. 7, 2005

(51) Int. Cl.
*A61N 1/365* (2006.01)
(52) U.S. Cl. ......................................................... 607/9
(58) Field of Classification Search .................. 607/14, 607/17, 25, 27–28, 9; 600/508–509, 515–516, 600/518
See application file for complete search history.

(56) References Cited

U.S. PATENT DOCUMENTS

| | | | | |
|---|---|---|---|---|
| 4,280,502 | A * | 7/1981 | Baker et al. | 607/14 |
| 5,213,098 | A | 5/1993 | Bennett et al. | |
| 5,683,431 | A | 11/1997 | Wang | |
| 5,702,427 | A * | 12/1997 | Ecker et al. | 607/28 |
| 6,263,242 | B1 | 7/2001 | Mika et al. | |
| 6,370,430 | B1 | 4/2002 | Mika et al. | |
| 6,424,866 | B2 | 7/2002 | Mika et al. | |
| 6,438,408 | B1 | 8/2002 | Mulligan et al. | |
| 6,501,989 | B1 | 12/2002 | Uhrenius et al. | |
| 2004/0049235 | A1 | 3/2004 | Deno et al. | |
| 2004/0220631 | A1 * | 11/2004 | Burnes et al. | 607/9 |
| 2004/0220640 | A1 * | 11/2004 | Burnes et al. | 607/28 |

FOREIGN PATENT DOCUMENTS

| | | |
|---|---|---|
| EP | 0 862 484 B1 | 5/1997 |
| WO | WO02053026 | 7/2002 |

\* cited by examiner

*Primary Examiner*—Robert E. Pezzuto
*Assistant Examiner*—Jessica L. Reidel
(74) *Attorney, Agent, or Firm*—Girma Wolde-Michael; Paul H. McDowall

(57) ABSTRACT

Techniques and apparatus for estimating the temporal refractory period of a heart, for adjusting a parameter for delivery of extra-systolic stimulation (ESS) therapy and for detecting an arrhythmia during delivery of ESS therapy In some aspects, probe pulses are periodically delivered to estimate the location of the end boundary of the refractory period, and accordingly estimate its length. In some embodiments, the parameter is adjusted based on estimated length of the refractory period. For example, an extra-systolic interval (ESI) for delivery of ESS is adjusted to be a fixed interval longer than estimated lengths of the refractory period. In other aspects, the parameter is adjusted based on a measured delay (or latency) between delivery of an ESS pulse and detection of an evoked response resulting from the pulse. Also, delays between delivery of an ESS pulse and detection of a subsequent depolarization are monitored to detect an arrhythmia.

41 Claims, 11 Drawing Sheets

REFRACTORY PERIOD TRACKING AND ARRHYTHMIA DETECTION

CROSS REFERENCE TO RELATED APPLICATIONS

The present patent application hereby cross-references and incorporates by reference the entire contents of the following applications, each of which is filed on even date herewith: non-provisional U.S. application Ser. No. 10/680, 462, entitled, "METHOD AND APPARATUS FOR CONTROLLING EXTRA-SYSTOLIC STIMULATION (ESS) THERAPY USING ISCHEMIA DETECTION," non-provisional U.S. application Ser. No. 10/680,49 entitled, "METHOD AND APPARATUS FOR OPTIMIZATION AND ASSESSMENT OF RESPONSE TO EXTRA-SYSTOLIC STIMULATION (ESS) THERAPY," non-provisional U.S. application Ser. No. 10/680,493 entitled, "EXTRA-SYSTOLIC STIMULATION THERAPY DELIVERY AND SENSING VIA DIFFERENT ELECTRODE SETS," non-provisional U.S. application Ser. No. 10/680, 695 entitled, "MULTIPLE PACING OUTPUT CHANNELS," non-provisional U.S. application Ser. No. 10/692, 990 entitled, "CARDIAC PACING MODALITY HAVING IMPROVED BLANKING, TIMING, AND THERAPY DELIVERY METHODS FOR EXTRA-SYSTOLIC STIMULATION PACING THERAPY," and non provisional U.S. application Ser. No. 10/703,956 entitled, "SECURE AND EFFICACIOUS THERAPY DELIVERY FOR AN EXTRA-SYSTOLIC STIMULATION PACING ENGINE."

TECHNICAL FIELD

The invention relates to cardiac pacing and, more particularly, to delivery of extra-systolic stimulation and arrhythmia detection.

BACKGROUND

The refractory period is an interval following a paced or spontaneous depolarization of the heart during which delivery of electrical stimulation to the heart is generally ineffective to cause a second depolarization. The refractory period is divided into an absolute refractory period during which no amount of electrical stimulation delivered to the heart will induce a corresponding depolarization, and relative refractory during which electrical stimulation delivered to the heart at an adequate energy level triggers a depolarization. As used herein, the term "refractory period" refers to a period of time that includes both the absolute and relative refractory periods.

A medical device, such as an implantable cardiac pacemaker, can be used to deliver extra-systolic stimulation to the heart. Typically, extra-systolic stimulation is delivered in the form of pulses to a chamber of the heart an extra-systolic interval (ESI) after a paced or spontaneous systolic depolarization of that chamber. Extra-systolic Stimulation (ESS) therapy involves delivery of extra-systolic stimulation after the refractory period, and results in a second depolarization without an attendant myocardial contraction, e.g., a non-systolic depolarization. Because it results in an electrical depolarization, the extra-systolic stimulation may be referred to as "excitatory." Delivery of extra-systolic stimulation within the refractory period does not result in a depolarization, and is therefore often referred to as non-excitatory stimulation (NES).

The second depolarization of the chamber resulting from delivery of a ESS therapy pulse effectively slows the heart rate from its spontaneous rhythm, allowing a greater time for filling of the chamber. Further, the second depolarization of the chamber causes a augmentation of contractile force of the chamber during the heart cycle following the one in which the ESS therapy pulse is applied. Increased filling and contractile force augmentation can lead to increased cardiac output, particularly when ESS therapy is delivered to one or more of the ventricles of the heart. NES is also believed to increase cardiac output, although to a lesser extent than ESS therapy, by increasing the sympathetic output to the heart. For this reason, ESS therapy and NES have been proposed as a therapy for patients with congestive heart failure (CHF) and/or left ventricular dysfunction (LVD).

The magnitude of the enhanced augmentation resulting from delivery of ESS therapy is strongly dependent on the timing of delivery of the extra-systolic pulse relative to the end of the refractory period. In particular, the magnitude of the enhanced augmentation decreases as the extra-systolic pulse is delivered further from the end, e.g., boundary, of the refractory period. The length of the refractory period can vary between patients, and changes for a particular patient over time based on the physiological condition and activities of the patient. For example, the length of the refractory period can change after resuscitation of the patient, while the patient is taking medications, and while the patient is exercising.

SUMMARY

In general, the invention is directed to techniques for estimating the length of the refractory period of a heart, for adjusting a parameter for delivery of extra-systolic stimulation (ESS) to the heart such as the extra-systolic interval (ESI), and for detecting an arrhythmia during delivery of ESS therapy.

Estimations of the refractory period length using the techniques described herein could be useful in a variety of contexts. For example, the estimated refractory period length could be monitored over time as an indicator of the progression of heart failure, response to medications, electrolyte disturbances, autonomic tone changes, and risk of arrhythmia. Estimated refractory period lengths could also be used to determine proper rate-response for rate-responsive pacing therapies, to set blanking periods and sensing thresholds used by pacemakers during delivery of pacing therapies, to identify the boundaries of ST segments within an electrogram signal, and to identify the refractory period boundary so that NES pulses can be delivered within the refractory period.

However, although the invention is not so limited, estimation of the length of the refractory period according to the invention is described herein in the context of adjustment of a parameter for delivery of ESS therapy pulses. More particularly, according to the invention, a medical device uses estimated lengths of the refractory period to adjust the ESI, e.g., to maintain a relationship between the ESI and the boundary of the refractory period despite changes in the length of the refractory period. For example, in exemplary embodiments a medical device adjusts the ESI to be a fixed interval longer than estimated lengths of the refractory period. By adjusting the ESI based on the estimated length of the refractory period, the medical device can maintain an effective level augmentation during delivery of ESS therapy despite changes in the length of the refractory period.

In some embodiments, a medical device periodically delivers probe pulses to the heart to estimate the location of the end, e.g., boundary, of the refractory period, and accordingly estimate its length. The medical device delivers probe pulses an interval after a systolic depolarization that is less than current ESI. The medical device increases the interval if the previous probe pulse fails to capture the heart, and decreases the interval if the previous probe pulse captured the heart.

In exemplary embodiments, the medical device determines whether two consecutive probe pulses did and did not capture the heart, respectively, and the estimates the length of the refractory period as a value between the intervals of the consecutive probe pulses. In some embodiments, in response to detecting that the refractory period length has changed, e.g., determining that both of two consecutive probe pulses either captured or did not capture the heart, the medical device delivers a series of probe pulses with increasing or decreasing intervals in order to relocate boundary of the refractory period and estimate its length. In some embodiments, the probe pulses of the series are delivered every cardiac cycle rather than periodically until the refractory period boundary is relocated.

In other embodiments, the ESI is adjusted based on a measured delay between delivery of an extra-systolic pulse and detection of an evoked response resulting from the pulse. The latency of the evoked response resulting from an extra-systolic pulse depends of the timing of the delivery of the pulse relative to the boundary of the refractory period. The latency decreases rapidly from the boundary to a break point. The latency does not vary substantially between pulses delivered at various intervals after the break point.

In some embodiments, a pair of probe pulses is delivered, each probe pulse delivered during a separate cardiac cycle. One of the probe pulses is delivered an interval after a systolic depolarization that is intended to place it between the refractory period and the latency break point. The other probe pulse is delivered an interval after a systolic depolarization that is intended to place it after the break point. The medical device compares the delays associated with the first and second probe pulses.

If the delay associated with the first probe pulse is less than the delay associated with the second probe pulse, the medical device determines that the refractory period length has increased such that the first probe pulse is within refractory period, and increases the interval for the probe pulses and the ESI. If the delays associated with the first and second probe pulses are substantially equal, the medical device determines that the refractory period length has decreased such that the first and second probe pulses were delivered after the break point, and decreases the intervals for the probe pulses and the ESI. If the delay associated with the first probe pulse is greater than the delay associated with the second probe pulse, the medical device determines that the refractory period length remains substantially unchanged because the first and second probe pulses were in fact delivered on their respective sides of the break point, and does not adjust the probe pulse intervals or the ESI.

In other embodiments, the medical device periodically delivers a probe pulse an interval after detection of systolic depolarizations intended to place the probe pulse between the refractory period boundary and the latency break point. The medical device measures the delay between delivery of the probe pulse and the resulting evoked response, and compares the delay to thresholds. If the delay is greater than a first threshold or no evoked response is detected, the medical device determines that the probe pulse was delivered either too close to or within the refractory period, and increases the probe pulse delivery interval and the ESI. If the delay is less than a second threshold, the medical device determines that the probe pulse was delivered too close to or after the latency break point, and decreases the probe pulse delivery interval and the ESI.

In some embodiments, a medical device monitors delays between delivery of ESS therapy pulses and detection of subsequent depolarizations to detect an arrhythmia of the heart. A medical device delivers ESS therapy pulses after the latency break point, and, consequently, the delays between ESS therapy pulses and the evoked responses resulting from delivery of ESS therapy pulses will generally be stable. If the medical device determines that the difference between a current delay and a previous delay is greater than a threshold value, e.g., the current depolarization occurs earlier than expected, the medical device can treat the determination as a detection of an arrhythmia or take action to determine if the early depolarization is the result of an arrhythmia. In some embodiments, the medical device compares delays resulting from coupled pulses, e.g., ESS therapy pulses delivered after an intrinsic systolic depolarization, with previous delays resulting from coupled pulses, and compares delays resulting from paired pulses, e.g., ESS therapy pulses delivered after a paced systolic depolarization, with previous delays resulting from paired pulses.

In some embodiments, the medical device suspends delivery of ESS therapy, e.g., for one cardiac cycle, in response to detection of an early depolarization. The medical device can more easily apply known arrhythmia detection algorithms while delivery of ESS therapy is suspended due to the absence of blanking intervals associated with delivery of ESS therapy pulses. In some embodiments, the medical device morphologically analyzes the early depolarization to determine whether the depolarization is the result of an arrhythmia. In some embodiments where the medical device delivers probe pulses to determine adjustments to the ESI of ESS therapy pulses, the medical device does not measure the delay during cardiac cycles during which a probe pulse is delivered.

In one embodiment, the invention is directed to a method in which a length of a refractory period of a heart is estimated, and a parameter for delivery of extra-systolic stimulation to the heart is set based on the estimated length.

In another embodiment, the invention is directed to a medical device comprising electrodes and a processor. The processor controls delivery of extra-systolic stimulation to a heart of a patient as a function of a parameter. The processor estimates a length of a refractory period of the heart, and sets a value for the parameter based on the estimated length.

In another embodiment, the invention is directed to a computer-readable medium containing instructions. The instructions cause a programmable processor to estimate a length of a refractory period of a heart, and set a parameter for delivery of extra-systolic stimulation to the heart based on the estimated length.

In another embodiment, the invention is directed to a method in which a systolic depolarization of a heart is detected, and a probe pulse is delivered an interval after detection of the systolic depolarization. Whether the probe pulse captured the heart is determined, and a length of a refractory period of the heart is estimated based on the determination.

In another embodiment, the invention is directed to a medical device comprising electrodes and a processor. The processor detects a systolic depolarization of a heart of a patient via the electrodes, controls delivery of a probe pulse via the electrodes an interval after detection of the systolic depolarization, determines whether the probe pulse captured the heart, and estimates a length of a refractory period of the heart based on the determination.

In another embodiment, the invention is directed to a computer-readable medium containing instructions. The instructions cause a programmable processor to detect a systolic depolarization of a heart, control delivery of a probe pulse an interval after detection of the systolic depolarization, determine whether the probe pulse captured the heart, and estimate a length of a refractory period of the heart based on the determination.

In another embodiment, the invention is directed to a method in which a delay between delivery of a pulse to a heart and detection of an evoked response resulting from delivery of the pulse is measured, and a parameter for delivery of extra-systolic stimulation to the heart is adjusted based on the delay.

In another embodiment, the invention is directed to a medical device comprising electrodes and a processor that controls delivery of pulses and extra-systolic stimulation to a heart of a patient and detect evoked response via the electrodes. The processor measures a delay between delivery of a pulse to the heart and detection of an evoked response resulting from delivery of the pulse, and adjusts a parameter for delivery of extra-systolic stimulation to the heart based on the delay.

In another embodiment, the invention is directed to a computer-readable medium containing instructions. The instructions cause a programmable processor to measure a delay between delivery of a pulse to a heart and detection of an evoked response resulting from delivery of the pulse, and adjust a parameter for delivery of extra-systolic stimulation to the heart based on the delay.

In another embodiment, the invention is directed to a method in which intervals between delivery of extra-systolic pulses to a heart and subsequent depolarizations of the heart are measured, and an arrhythmia of the heart is detected based on the intervals.

In another embodiment, the invention is directed to a medical device comprising electrodes and a processor that controls delivery of extra-systolic pulses to a heart and detects depolarizations of the heart via the electrodes. The processor measures intervals between delivery of extra-systolic pulses and subsequent depolarizations, and detects an arrhythmia of the heart based on the intervals.

In another embodiment, the invention is directed to a computer-readable medium containing instructions. The instructions cause a programmable processor to measure intervals between delivery of extra-systolic pulses to a heart and subsequent depolarizations of the heart, and detects an arrhythmia of the heart based on the intervals.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
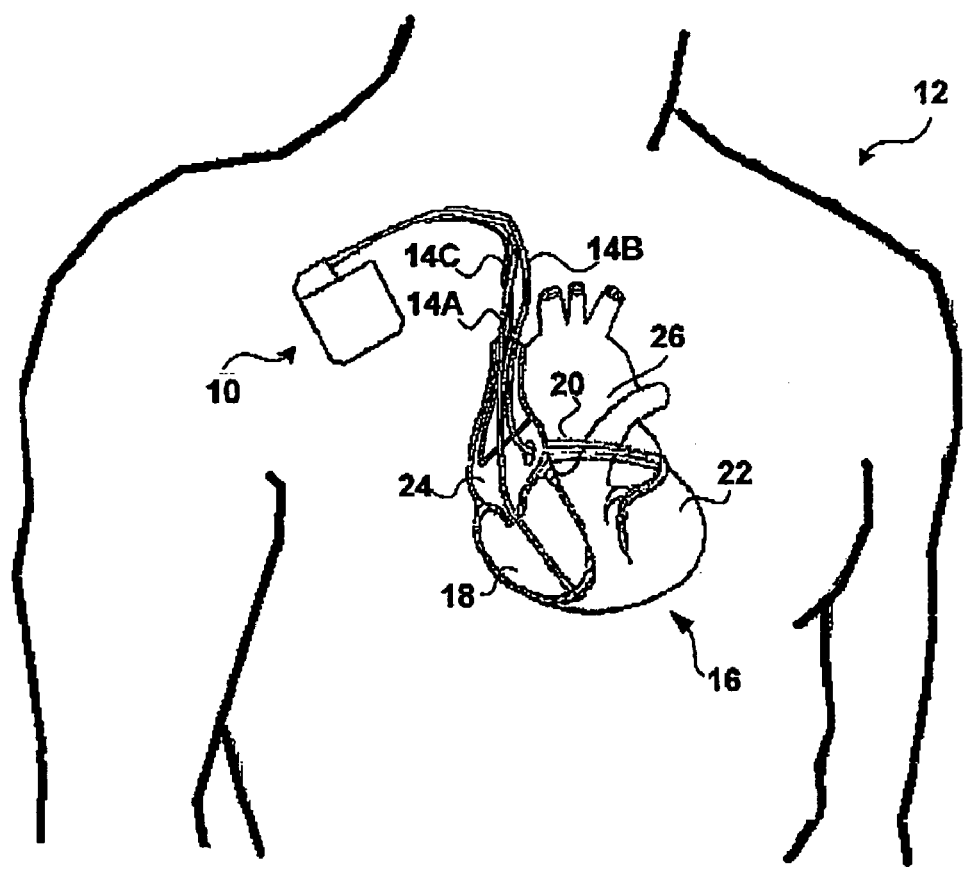
FIG. 1 is a conceptual diagram illustrating an exemplary implantable medical device that delivers ESS therapy implanted within a patient.

FIG. 1 is a conceptual diagram illustrating an exemplary implantable medical device (IMD) 10 implanted within patient 12. IMD 10 delivers ESS therapy to heart 16 of patient 12. In the illustrated embodiment, IMD 10 takes the form of a multi-chamber cardiac pacemaker.

IMD 10 is coupled to leads 14A, 14B and 14C (collectively "leads 14") that extend into the heart 16 of patient 12. More particularly, right ventricular (RV) lead 14A extends through one or more veins (not shown), the superior vena cava (not shown), and right atrium 24, and into right ventricle 18. Left ventricular (LV) coronary sinus lead 14B extends through the veins, the vena cava, right atrium 24, and into the coronary sinus 20 to a point adjacent to the free wall of left ventricle 22 of heart 16. Right atrial (RA) lead 14C extends through the veins and vena cava, and into the right atrium 24 of heart 16.

Each of leads 14 includes electrodes (not shown in FIG. 1). IMD 10 delivers ESS therapy pulses to one or more of chambers 18, 22, and 24 via electrodes carried by one or more of leads 14. In some embodiments, IMD 10 also delivers pacing pulses to one or more of chambers 18, 22, and 24 via electrodes carried by one or more of leads 14. In various embodiments, ESS therapy and pacing pulses have a single phase, are biphasic, or are multiphasic. IMD 10 also senses electrical activity within chambers 18, 22, and 24 via electrodes carried on leads 14. The electrodes on leads 14 are unipolar or bipolar, as is well known in the art.

IMD 10 delivers ESS therapy pulses to one or more of chambers 18, 22, and 24 an ESI after an intrinsic or paced depolarization of that chamber. In various embodiments, IMD 10 delivers ESS therapy pulses continuously, periodically, in response to user activation, as a function of measured physiological parameters, or the like. Exemplary techniques for delivering and controlling delivery of ESS therapy are described in U.S. Pat. No. 5,213,098 and prior, co-pending non-provisional U.S. patent application Ser. No. 10/322,792 filed 28 Aug. 2002 and its corresponding PCT application (publication no. WO 02/053026) by Deno et al., both of which are hereby incorporated herein by reference, discloses a family of implantable medical devices for delivering post extra-systolic augmentation stimulation.

According to the invention, IMD 10 estimates a length of the refractory period of heart 16, and adjusts the ESI based on estimated length, e.g., to maintain a relationship between the ESI and the boundary of the refractory period despite changes in the length of the refractory period. For example, in exemplary embodiments IMD 10 adjusts the ESI to be a fixed interval longer than estimated lengths of the refractory period. By adjusting the ESI based on the estimated length of the refractory period, the IMD 10 can maintain an effective level augmentation during delivery of ESS therapy despite changes in the length of the refractory period.

In some embodiments, as will be described in greater detail below, IMD 10 periodically delivers probe pulses to heart 16 via the electrodes carried on leads 14 to estimate the location of the end, e.g., boundary, of the refractory period, and accordingly estimate its length. IMD 10 estimates the location of the boundary of the refractory period based on whether the probe pulses capture heart 16. IMD 10 delivers probe pulses at various intervals after systolic depolarizations that are less than a current ESI to detect the boundary of the refractory period. In exemplary embodiments, IMD 10 delivers the probe pulses with substantially the same amplitude, width and shape as ESS therapy pulses.

In other embodiments, as will be described in greater detail below, IMD 10 adjusts the ESI based on a measured delay between delivery of an extra-systolic pulse, e.g., a probe pulse and detection of an evoked response resulting from the pulse. IMD 10 detects evoked responses resulting from ESS therapy pulses via electrodes carried on leads 14. IMD 10 may employ a variety of techniques to detect evoked responses despite the application of blanking intervals following delivery of ESS therapy pulses, as will be described in greater detail below.

In some embodiments, IMD 10 monitors delays between delivery of ESS therapy pulses and detection of subsequent depolarizations to detect an arrhythmia of heart 16. As will be described in greater detail below, the delays between ESS therapy pulses and the evoked responses resulting from delivery of ESS therapy pulses will generally be stable. IMD 10 detects an arrhythmia by detecting instability in the lengths of the delays. In exemplary embodiments, IMD 10 suspends delivery of ESS therapy, e.g., for one cardiac cycle, in response to detection of instability in the delays in order to, for example, apply an arrhythmia detection algorithm in order to determine if the instability is caused by an arrhythmia.

The configuration of IMD 10 and leads 14 illustrated in FIG. 1 is merely exemplary. In various embodiments, IMD 10 is coupled to any number of leads 14 that extend to a variety of positions within or outside of heart 16. For example, in some embodiments, IMD 10 is coupled to a lead 14 that extends to left atrium 26 of heart 16, or epicardial leads instead of or in addition to the transvenous leads 14 illustrated in FIG. 1. Further, the invention is not limited to IMDs, but may instead include an external medical device that delivers ESS therapy pulses to heart 16. Such medical device can deliver pacing and ESS therapy pulses to heart 16 via percutaneous leads that extend through the skin of patient 12 to a variety of positions within or outside of heart 16, or transcutaneous electrodes placed on the skin of patient 12.

Figure 2:
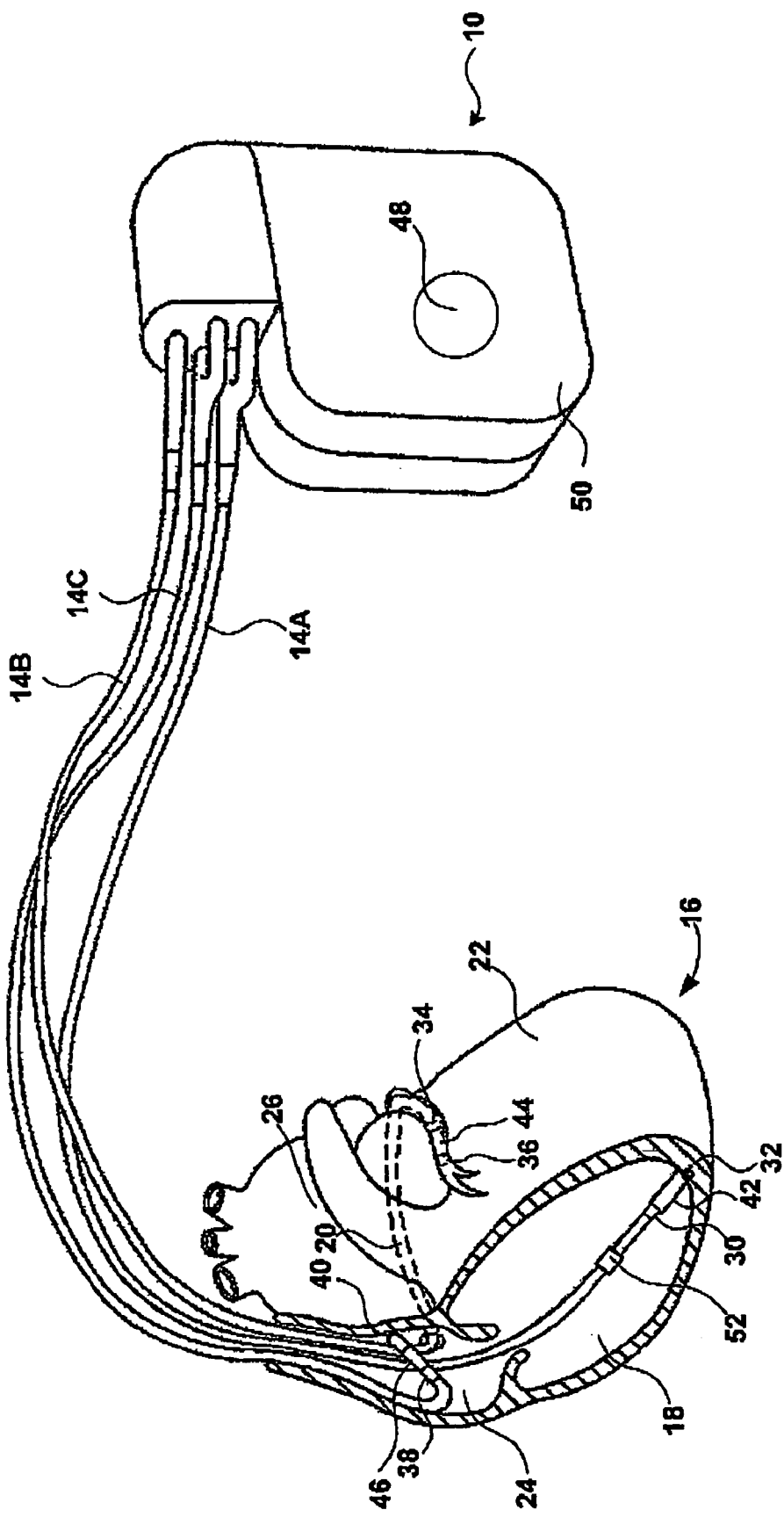
FIG. 2 is conceptual diagram further illustrating the implantable medical device of FIG. 1 and the heart of the patient.

FIG. 2 is a conceptual diagram further illustrating IMD 10 and heart 16 of patient 12. In some embodiments, each of leads 14 includes an elongated insulative lead body carrying a number of concentric coiled conductors separated from one another by tubular insulative sheaths. In the illustrated embodiment, bipolar electrode pairs 30 and 32, 34 and 36, and 38 and 40 are located adjacent distal end of leads 14A, 14B and 14C, respectively. In exemplary embodiments, electrodes 30, 34 and 38 take the form of ring electrodes, and electrodes 32, 36 and 40 take the form of extendable helix tip electrodes mounted retractably within insulative electrode heads 42, 44 and 46, respectively. Each of the electrodes 30–40 is coupled to one of the coiled conductors within the lead body of its associated lead 14.

IMD 10 senses electrical signals attendant to the depolarization and repolarization of heart 16 via selected ones of electrodes 30, 32, 34, 36, 38 and 40. The electrical signals are conducted to IMD 10 via leads 14. IMD 10 also delivers ESS therapy pulses, and in some embodiments pacing pulses and probe pulses, via one or more of the bipolar electrode pairs. In the illustrated embodiment, IMD 10 also includes an indifferent housing electrode 48, formed integrally with an outer surface of the hermetically sealed housing 50 of IMD 10. In such embodiments, IMD 10 is capable of using any of electrodes 30, 32, 34, 36, 38 and 40 for unipolar sensing or pulse delivery in combination with housing electrode 48. In some embodiments, IMD 10 delivers defibrillation and/or cardioversion shocks to heart 16 via elongated coil defibrillation electrodes (not shown) carried on one or more of leads 14.

In some embodiments, IMD 10 also includes a sensor 52 that generates a signal as a function of a physiological parameter of patient 12. As will be described in greater detail below, IMD 10 processes the output of sensor 52 to determine whether probe pulses captured heart 16. In exemplary embodiments, sensor 52 takes the form of an intracardiac pressure sensor. In such embodiments, IMD 10 processes the signal to measure of the derivative of the intracardiac pressure, which reflects augmentation of heart 16. In some embodiments, sensor 52 is a capacitive absolute pressure sensor, as described in U.S. Pat. No. 5,564,434 to Halperin, et al., hereby incorporated by reference herein in its entirety, a piezoelectric crystal, or piezoresistive pressure transducer.

The invention is not, however, limited to any particular kind of sensor 52, to any particular location of sensor 52, or any particular physiological parameter. For example, in some embodiments sensor 52 takes the form of an accelerometer located on the distal end of lead 14B to measure isovolumetric acceleration, or an oximeter located on lead 14A to measure oxygen saturation as a surrogate for flow changes. In each of these cases, the measured parameter reflects the intensity of augmentation. Further the invention is not limited to embodiments of IMD 10 that include a sensor that generates a signal as a function of a physiological parameter of patient 12.

Figure 3:
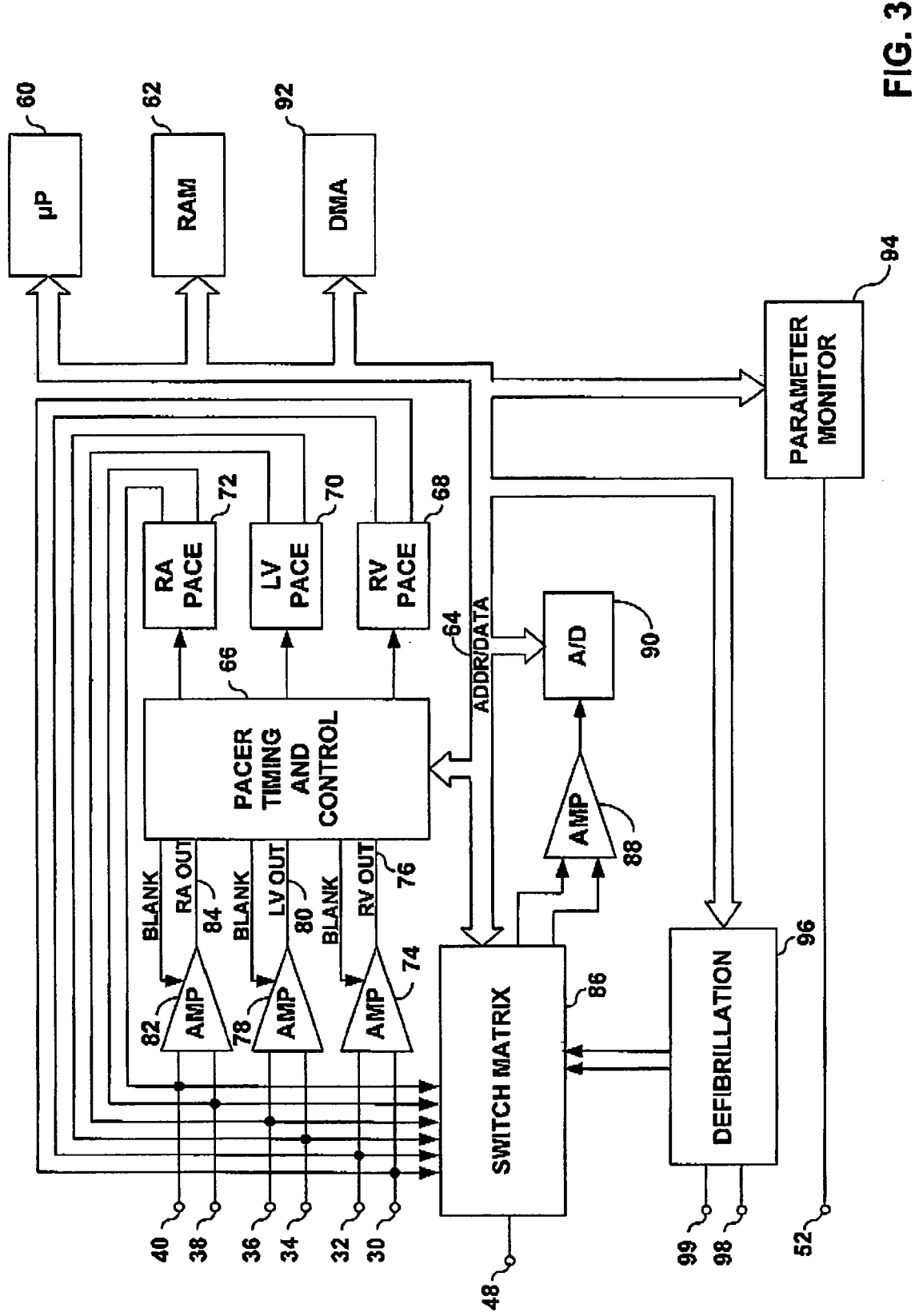
FIG. 3 is a functional block diagram further illustrating the implantable medical device of FIG. 1.

FIG. 3 is a functional block diagram of IMD 10. In the illustrated embodiment, IMD 10 takes the form of a multi-chamber pacemaker having a microprocessor-based architecture. However, this diagram should be taken as exemplary of the type of device in which various embodiments of the present invention may be embodied, and not as limiting, as it is believed that the invention may be practiced in a wide variety of device implementations.

IMD 10 includes a microprocessor 60. Microprocessor 60 executes program instructions stored in a memory, e.g., a computer-readable medium, such as a ROM (not shown), EEPROM (not shown), and/or RAM 62 which control microprocessor 60 to perform the functions ascribed to microprocessor 50 herein. Microprocessor 60 is coupled to, e.g., to communicate with and/or control, various other components of IMD 10 via an address/data bus 64.

IMD 10 senses electrical activity within heart 16, delivers ESS therapy pulses and probe pulses to heart 16, and, in some embodiments, delivers pacing pulses to heart 16. Pacer/timing control circuitry 66 controls delivery of ESS therapy, probe, and pacing pulses by one or more of output circuits 68-72 via electrodes 30–40. Specifically, output circuit 68 is coupled to electrodes 30 and 32 to deliver pulses to right ventricle 18, output circuit 70 is coupled to electrodes 34 and 34 to deliver pulses to left ventricle 22, and output circuit 72 is coupled to electrodes 38 and 40 to deliver pulses to right atrium 24. Output circuits 68–72 include known circuitry for storage and delivery of energy in the form of pulses, such as switches, capacitors, and the like.

Pacer timing/control circuitry 66 includes programmable digital counters that control the timing of delivery of pulses the values of which are set based on information received from microprocessor 60 via data bus 64. In exemplary embodiments, a counters maintained by circuitry 66 reflect the ESI and the intervals between detection of a systolic depolarization and delivery of a probe pulse. Circuitry 66 also preferably controls escape intervals associated with pacing, such as atrial and/or ventricular escape intervals associated with a selected mode of pacing. In some embodiments, IMD 10 delivers cardiac resynchronization therapy (CRT), and circuitry 66 controls a V—V interval for delivery of bi–ventricular pacing.

Pacer/timing control circuitry 66 resets interval counters upon detection of R-waves or P-waves, or generation of pacing pulses, and thereby controls the basic timing of ESS therapy and cardiac pacing functions. Intervals defined by pacing circuitry 66 also include refractory periods during which sensed R-waves and P-waves are ineffective to restart timing of escape intervals. The durations of these intervals are determined by microprocessor 50 in response to data stored in RAM 62, and are communicated to circuitry 66 via address/data bus 64. The amplitude of the pulses, e.g., the energy stored in capacitors of output circuits 68–72, is also determined by circuitry 66 under control of microprocessor 60.

Microprocessor 60 operates as an interrupt driven device, and is responsive to interrupts from pacer timing/control circuitry 66 corresponding to the occurrence of sensed P-waves and R-waves and corresponding to the generation of cardiac pacing pulses. Those interrupts are provided via data/address bus 64. Any necessary mathematical calculations to be performed by microprocessor 60 and any updating of the values or intervals controlled by pacer timing/control circuitry 66 take place following such interrupts.

IMD 10 senses electrical activity within heart 16 via sense amplifiers 74, 78 and 82, which sense electrical activity within right ventricle 18, left ventricle 22, and right atrium 24, respectively. Sense amplifiers 74, 78 and 82 take the form of automatic gain controlled amplifiers providing an adjustable sensing threshold as a function of the measured P-wave or R-wave amplitude. Sense amplifiers 74, 78 and 82 generate signals on RV out line 76, LV out line 80 and RA out line 84, respectively, whenever the signal sensed between the electrodes coupled thereto exceeds the present sensing threshold. Thus, sense amplifiers 74, 78 and 82 are used to detect intrinsic right ventricular, left ventricular, and right atrial depolarizations, e.g., R-waves and P-waves, respectively.

In some embodiments, sense amplifiers 74, 78 and 82 are also used to detect evoked responses resulting from delivery of ESS therapy or probe pulses. However, detection of evoked responses is complicated by the blanking of sense amplifiers 74, 78 and 82 following delivery of a pulse via the electrodes coupled to that amplifier. In some embodiments, IMD 10 delivers biphasic pulses to heart 16, which result in less polarization of cardiac tissue near the electrodes used to the pulse. In embodiments, wherein IMD 10 delivers biphasic pulses, pacer timing/control circuit 66 can apply shorter blanking intervals to sense amplifiers 74, 78 and 82, allowing for more effective detection of evoked responses via sense amplifiers 74, 78 and 82. In other embodiments, sense amplifiers 74, 78 and 82 detect electrical activity, e.g., an evoked response, within a chamber of heart 16 via a different set of electrodes than is used to deliver ESS therapy, probe and pacing pulses to that chamber as described in commonly assigned U.S. application Ser. No. 10/680,695 by Chris Zillmer et al., which is hereby incorporated herein by reference in its entirety. In still other embodiments, microprocessor 60, or a separate digital signal processor (DSP) (not shown), applies known digital signal processing techniques to an electrogram signal detected by selected electrodes in order to detect evoked responses despite the presence of noise causes by myocardial tissue polarization.

Switch matrix 86 is used to select which of the available electrodes 30–40, 48, 98 and 99 are coupled to wide band (0.5–200 Hz) amplifier 88 for use in digital signal analysis. Selection of electrodes is controlled by microprocessor 60 via data/address bus 64, and the selections may be varied as desired. The analog signals derived from the electrodes selected by switch matrix 86 and amplified by amplifier 88 are converted to a multi-bit digital signal by A/D converter 90, and the digital signal is digitally processed by microprocessor 60. In some embodiments, the digital signal is stored in RAM 62 under control of direct memory access circuit (DMA) 92 for later analysis by microprocessor 60.

In some embodiments, IMD 10 detects ventricular and/or atrial tachycardias or fibrillations of heart 16 using tachycardia and fibrillation detection techniques and algorithms known in the art. For example, the presence of a ventricular or atrial tachycardia or fibrillation can be confirmed by detecting a sustained series of short R—R or P—P intervals of an average rate indicative of tachycardia, or an unbroken series of short R—R or P—P intervals. In some embodiments, microprocessor 60 digitally analyzes an electrogram signal using known techniques to detect ventricular and/or atrial tachycardias or fibrillations of heart 16. In still other embodiments, as will be described in greater detail below, microprocessor 60 applies a morphological analysis to some depolarizations detected subsequent to delivery of ESS therapy pulses to detect an arrhythmia. The morphological analysis can include, for example, an analysis of the width of the depolarization and/or a wavelet analysis.

IMD 10 is also capable of delivering one or more anti-tachycardia pacing (ATP) therapies to heart 16, and/or defibrillation or cardioversion pulses to heart 16 via one or more of electrodes 30–40, 48, 98 and 99. Electrodes 98 and 99 are coupled to defibrillation circuit 96, which delivers defibrillation and/or cardioversion pulses under the control of microprocessor 60. Defibrillation circuit 96 includes energy storage circuits such as capacitors, switches for coupling the storage circuits to electrodes 98 and 99, and logic for controlling the coupling of the storage circuits to the electrodes to create pulses with desired polarities and shapes. Microprocessor 60 may employ an escape interval counter to control timing of such defibrillation pulses, as well as associated refractory periods. The invention is not limited to embodiments where IMD 10 includes defibrillator functionality.

In the illustrated example, IMD 10 also includes a parameter monitor circuit 94. Parameter monitor circuit 94 processes the signal received from sensor 52, and provides a result of the processing to microprocessor 60 for use in determining whether a probe pulse captured heart 16. In exemplary embodiments where sensor 52 is an intracardiac pressure sensor, monitor circuit 94 processes the pressure signal to provide information indicating the derivative of the pressure signal, which indicates the extent of augmentation, to microprocessor 60.

Although described herein in the context of a microprocessor-based pacemaker embodiment IMD 10, the invention may be embodied in various implantable medical devices that include one or more processors, which may be microprocessors, DSPs, field-programmable gate arrays (FPGAs), application specific integrated circuits (ASICs), or other digital logic circuits.

Figure 4:
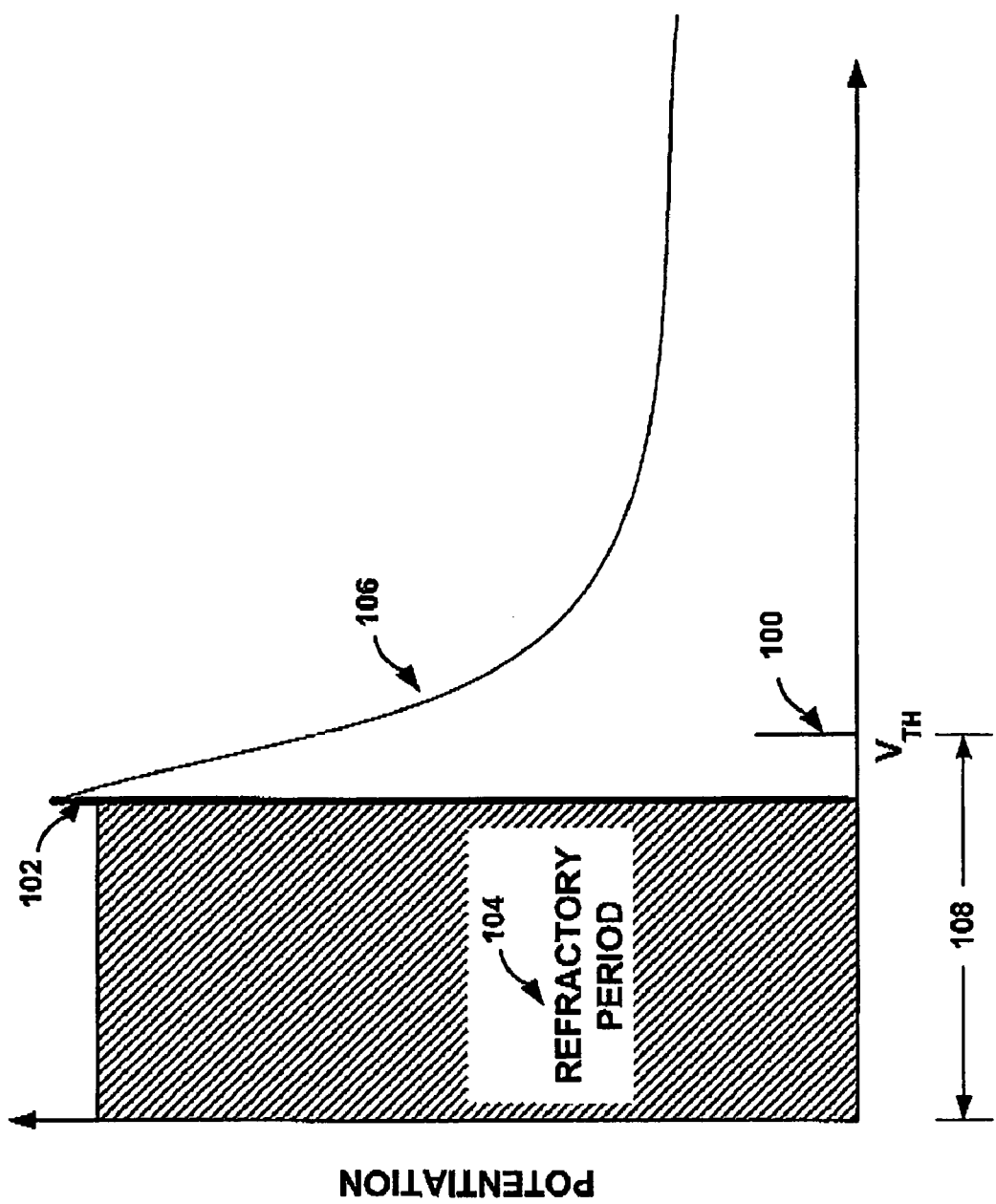
FIG. 4 is a diagram illustrating the relationship between the extent of augmentation and the timing of delivery of an extra-systolic pulse relative to the boundary of the refractory period.

FIG. 4 is a diagram illustrating the relationship between the extent of augmentation and the timing of delivery of an extra-systolic pulse 100 relative to the boundary 102 of the refractory period 104. Specifically, FIG. 4 includes a curve 106, which illustrates relationship between the extent of augmentation and the time of delivery of a pulse during a cardiac cycle. Refractory period 104 is typically less than 100 milliseconds (ms) in duration, and begins following a paced or spontaneous systolic depolarization of heart 16. Pulses delivered within refractory period 104 result in no augmentation.

As shown in FIG. 4, delivery of ESS therapy pulse 100 an ESI 108 after a paced or intrinsic depolarization results in significant augmentation. However, physiological conditions of patient 12 may result in lengthening or shortening of refractory period 104, i.e., movement of boundary 102 and curve 106. If boundary 102 and curve 106 move, the augmentation resulting from delivery of ESS therapy pulse 100 according to ESI 108 can be diminished or, if ESS therapy pulse 100 is delivered during refractory period 104, lost.

Figure 5:
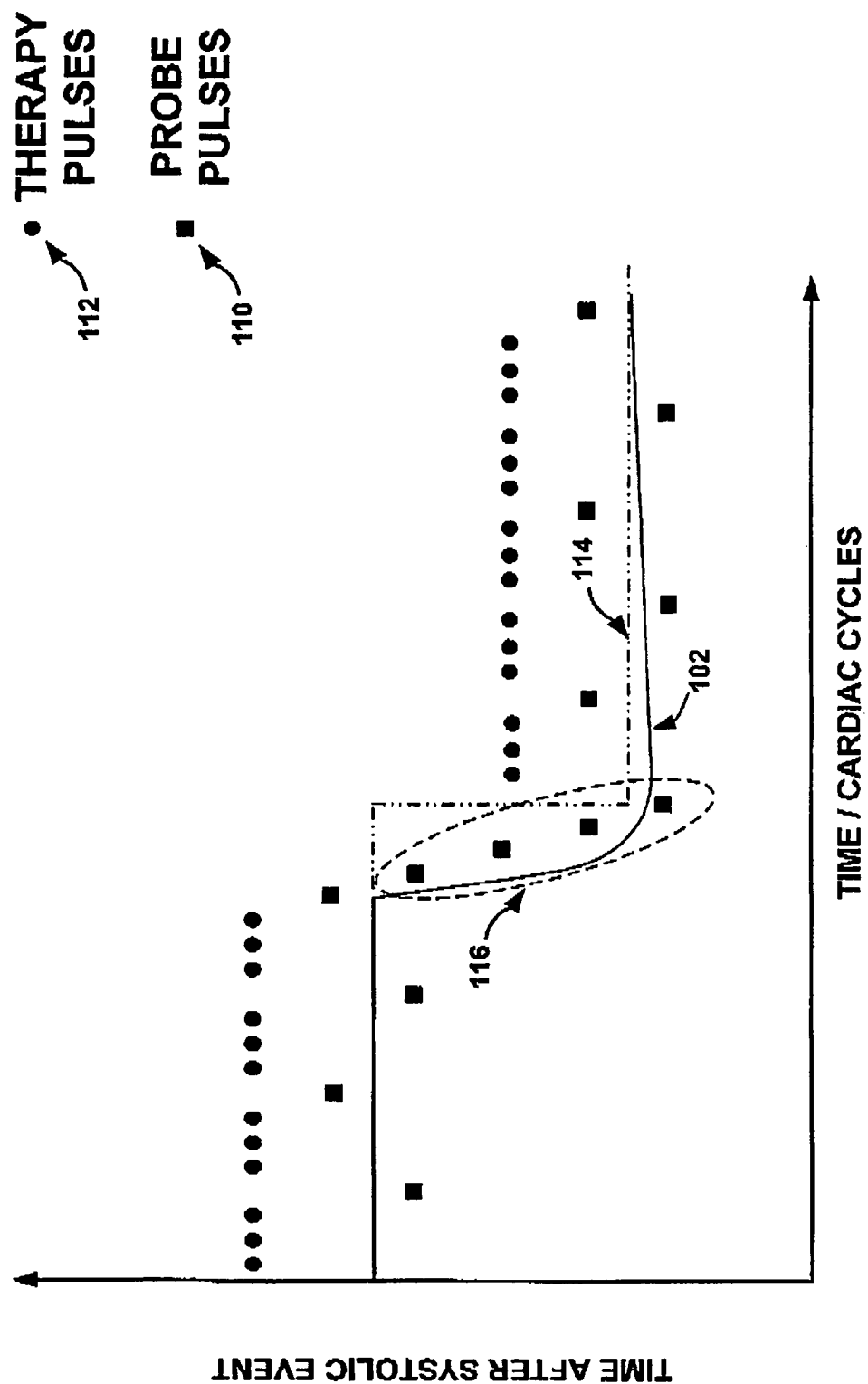
FIG. 5 is a timing diagram illustrating an example mode of operation of the implantable medical device of FIG. 1 to estimate the length of the refractory period and set an extra-systolic interval for delivery of ESS therapy based on the estimated length.

FIG. 5 is a timing diagram illustrating an example mode of operation of IMD 10 to estimate the length of the refractory period and set the ESI based on the estimated length. In particular, FIG. 5 illustrates a mode of operation in which IMD 10 delivers a probe pulse 110 every N cardiac cycles to detect the boundary 102 of refractory period 104 (FIG. 4). In the illustrated example, N is equal to 4. Therapy pulses 112, e.g., ESS therapy pulses, are delivered the ESI after detection of a systolic depolarization during cardiac cycles in which a probe pulse 110 is not delivered.

As shown in FIG. 5, IMD 10 increases the interval for delivery of a subsequent probe pulse 110 upon detection that the current probe pulse 110 did not capture heart 16, and decreases the interval for delivery of a subsequent probe pulse 110 upon detection that the current probe pulse 110 captured heart 16. IMD 10 estimates the length of the refractory period based on a determination that consecutive probe pulses 110 transition between capturing and not capturing heart 16. IMD sets an estimated length 114 of the refractory period at a value between the intervals at which transitioning probe pulses were delivered. In the illustrated example, IMD 10 sets estimated length 114 at the average of the two intervals.

In the illustrated example, the ESI is a set an amount of time longer than estimated refractory period length 114, such as 40 milliseconds. The increases and decreases in the interval for delivery of probe pulses 110 can be a constant value, such as 20 ms. As shown in FIG. 5, IMD 10 maintains the current value of the ESI and estimated refractory period length 114 so long as probe pulses 110 continue to transition between capture and non-capture.

At circled area 116 of FIG. 5, refractory boundary 102 moves, and, consequently, a probe pulse 110 that was expected to capture heart 16 does not capture heart 16. IMD 10 decreases the interval for delivery of each of a series of probe pulses 110 until one of the probe pulses 110 captures heart 16. When the probe pulse 110 captures heart 16, IMD 10 detects a capture/non-capture transition, and sets estimated refractory period length 114 and the ESI as described above. In general, where an expected capture or non-capture does not occur, IMD 10 decreases or increases the interval for delivery of successive probe pulses 110 until another capture/non-capture transition is detected, e.g., until boundary 102 is found. In some embodiments, as illustrated in FIG. 5, IMD 10 delivers probe pulses 110 every cardiac cycle after an expected capture or non-capture does not occur in order to more quickly relocate boundary 102.

In some embodiments, IMD 10 applies lock-outs to avoid arriving at unsafe or undesirable ESI via the described techniques. For example, IMD 10 can prevent the ESI from exceeding or falling below certain values, such as 400 ms and 180 ms, respectively. Further, in some embodiments, IMD 10 prevents the probe pulse delivery interval and ESI from being too close to each other as IMD 10 relocates boundary 102 by, for example, adjusting the ESI to be at least 30 ms greater than the probe pulse interval.

In some embodiments, IMD 10 determines whether a probe pulse captures heart 16 by detecting evoked responses via sense amplifiers 74, 78 and 82 or digital processing of an electrogram signal. In other embodiments, IMD 10 determines whether a probe pulse captured the heart by comparing the augmentation resulting from consecutive probe pulses 110. If IMD 10 determines that a probe pulse 110 intended to not capture heart 16 resulted in greater augmentation than a probe pulse 110 intended to capture heart 16, IMD 10 determines that the probe pulse 110 intended not to capture did capture heart. Further, if IMD 10 determines that consecutive probe pulses resulted in substantially similar augmentation, IMD 10 determines that a probe pulse 110 intended to capture heart 16 did not capture heart 16.

Figure 6:
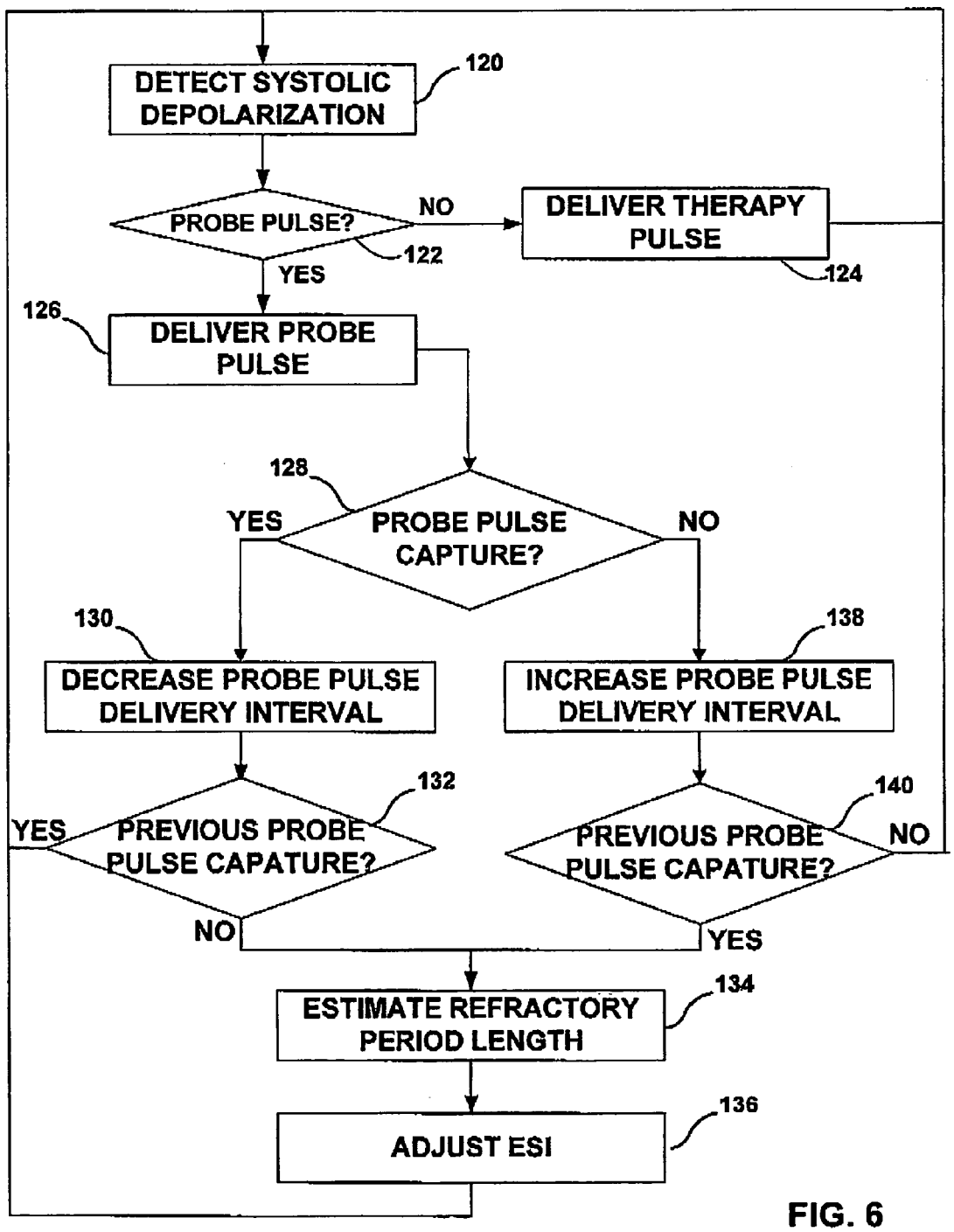
FIG. 6 is a flow diagram further illustrating the example mode of operation of FIG. 5.

FIG. 6 is a flow chart further illustrating the mode of operation of FIG. 5. IMD 10 detects a systolic depolarization of heart 16 (120), and determines whether a probe pulse 110 is scheduled for delivery during the current cardiac cycle (122). If delivery of a probe pulse 110 is not scheduled for the current cardiac cycle, IMD 10 delivers a therapy pulse 112 the current ESI after detection of the systolic depolarization (124).

If delivery of a probe pulse 110 is scheduled for this cardiac cycle, IMD 10 delivers the probe pulse 110 an interval after detection of the systolic depolarization that is determined based on the interval for a previous probe pulse 110 and whether the previous probe pulse 110 captured heart 16 (126). IMD 10 determines whether the current probe pulse 110 captured heart 16 (128). If the probe pulse 110 captured heart 16, IMD 10 decreases the probe pulse delivery interval for delivery of a subsequent probe pulse 110 (130). If IMD 10 determines that the previous probe pulse 110 did not capture heart 16 (132), IMD 10 identifies a capture/non-capture transition, sets an estimated refractory period length 114 at a value between the delivery intervals for the previous and current probe pulses 110 (134), and sets the ESI to be an amount of time greater than the estimated refractory period length 114 (136).

If the current probe pulse 110 did not capture heart 16, IMD 10 increases the probe pulse delivery interval for delivery of a subsequent probe pulse 110 (138). If IMD 10 determines that the previous probe pulse 110 did capture heart 16 (140), IMD 10 identifies a capture/non-capture transition, sets an estimated refractory period length 114 at a value between the delivery intervals for the previous and current probe pulses 110 (134), and sets the ESI to be an amount of time greater than the estimated refractory period length 114 (136).

Figure 7:
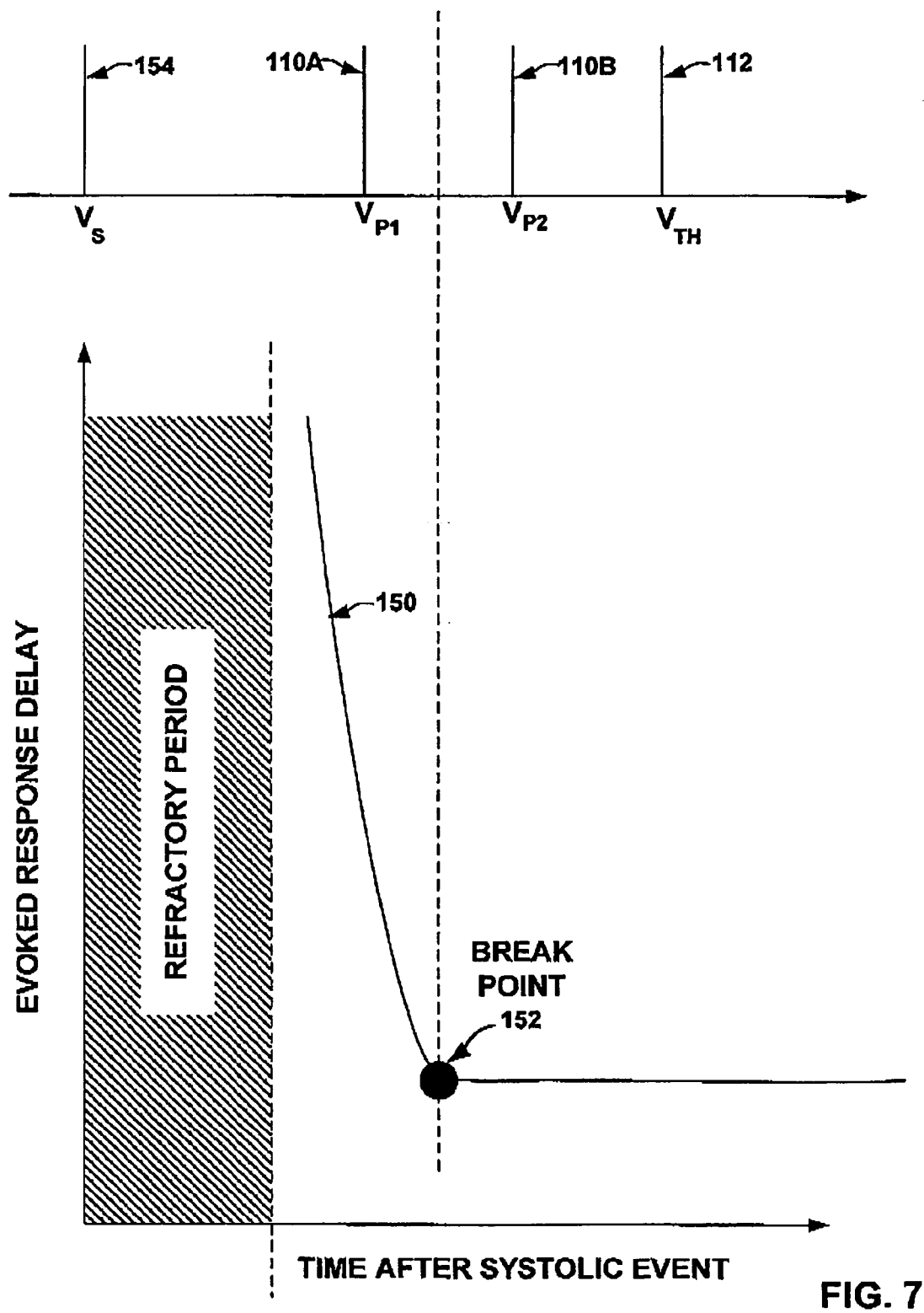
FIG. 7 is a timing diagram illustrating an example mode of operation of the implantable medical device of FIG. 1 to adjust the extra-systolic interval based on delays between delivery of extra-systolic stimulation pulses and resulting evoked responses.

FIG. 7 is a timing diagram illustrating an example mode of operation of IMD 10 to adjust the ESI based on delays between delivery of extra-systolic pulses and resulting evoked responses. As illustrated by FIG. 7, the latency of the evoked response resulting from an extra-systolic pulse depends of the timing of the delivery of the pulse relative to the boundary of the refractory period. Specifically, latency curve 150 illustrates an example relationship between evoked response latency and the time at which an extra-systolic pulse is delivered relative to the boundary of the refractory period. As illustrated in FIG. 7, the latency decreases rapidly from an initial maximum at the refractory period boundary to a break point 152. The latency does not vary substantially between pulses delivered at various intervals after break point 152.

In exemplary embodiments, IMD 10 delivers probe pulses 110, measures the delays between delivery of the probe pulses 110 and associated evoked responses, and adjusts the ESI and intervals for delivery of probe pulses based on the delays. In exemplary embodiments, IMD 10 delivers a probe pulse 110 every N cardiac cycles. In some embodiments, IMD 10 delivers a first probe pulse 110A a first interval after detection of a first systolic depolarization 154, and a second probe pulse 110B a second interval after detection of a second systolic depolarization 154. IMD 10 compares the delays associated with the first and second probe pulses 110 to determine whether the ESI and probe pulse delivery intervals need to be adjusted. IMD 10 similarly adjusts the delivery intervals for probe pulses 110 and the ESI in order to maintain an interval between the refractory period boundary and ESS therapy pulses 112.

In exemplary embodiments, the delivery intervals and ESI are adjusted until the first pulse 110A occurs between the refractory period boundary and break point 152, and second pulse 110B occurs after break point 152. If the delay associated with first probe pulse 110A is less than the delay associated with second probe pulse 110B, IMD 10 determines that first probe pulse 110A is within the refractory period and increases the interval for the probe pulses and the ESI. If the delays associated with the first and second probe pulses 110 are substantially equal, IMD 10 determines that the first and second probe pulses 110 were both delivered after break point 152, and decreases the intervals for the probe pulses and the ESI. If the delay associated with the first probe pulse 110A is greater than the delay associated with the second probe pulse 110B, IMD 10 determines that first and second probe pulses 110 were in fact delivered on their respective sides of break point 152, and does not adjust the probe pulse intervals or the ESI.

Figure 8:
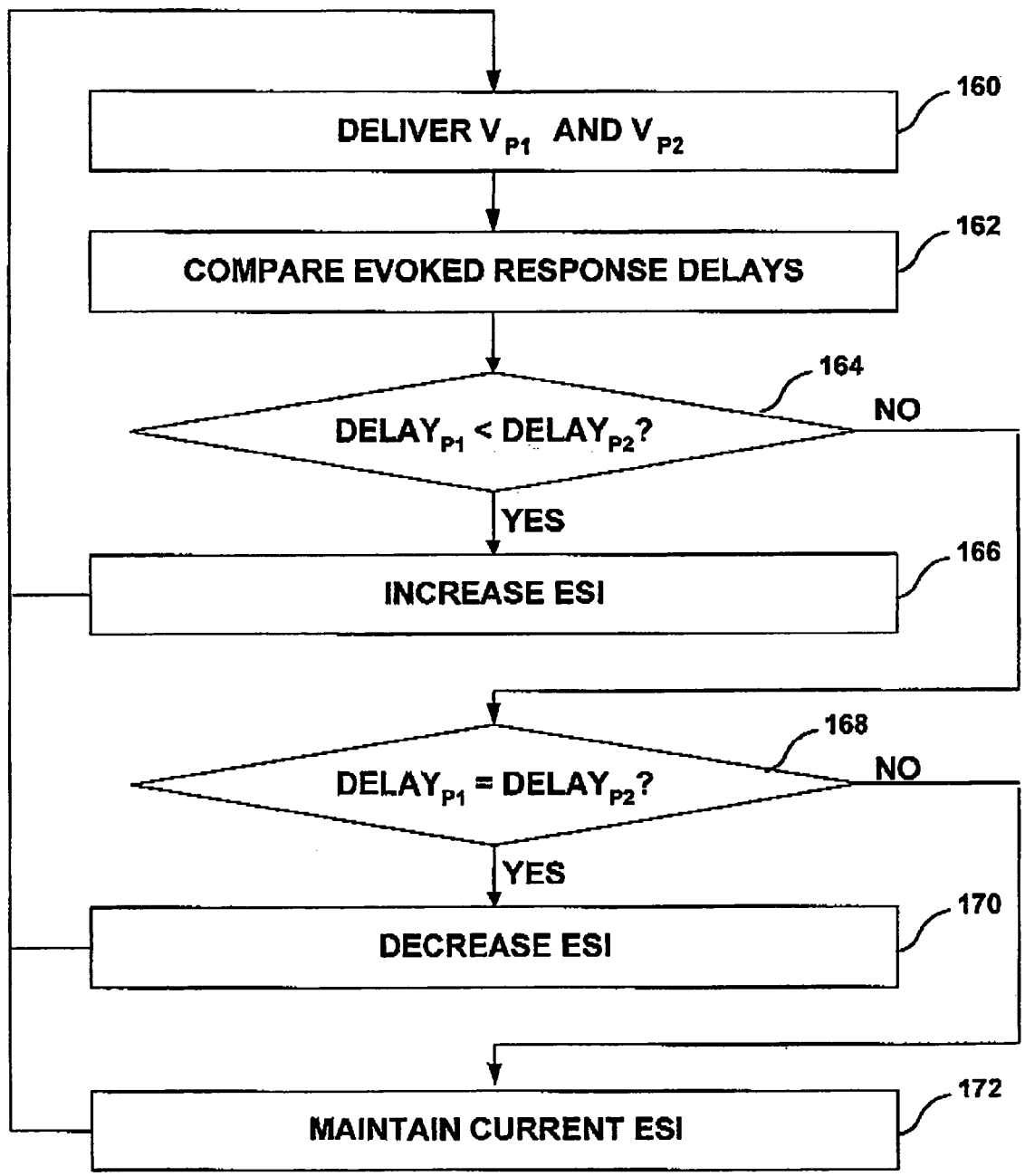
FIG. 8 is a flow diagram further illustrating the example mode of operation of FIG. 7.

FIG. 8 is a flow diagram further illustrating the example mode of operation of FIG. 7. IMD 10 delivers the first and second probe pulses 110A and 110B at respective probe pulse delivery intervals during respective cardiac cycles (160), and compares the delays of respective evoked responses detected subsequent to delivery of the probe pulses 110 (162). The probe pulse delivery interval for the first probe pulse 110A is less than the probe pulse delivery interval of the second probe pulse 110B by, for example, 20 ms.

If IMD 10 determines that the delay between of first probe pulse 110A and its resulting evoked response is less than the delay between second probe pulse 110B and its resulting evoked response (164), IMD 10 increases the ESI and the probe pulse delivery intervals by, for example, 10 ms (166). If IMD 10 determines that the delays between the first and second probe pulses 100 and their resulting evoked responses are substantially equal (168), IMD 10 decreases the ESI and the probe pulse delivery intervals by, for example, 10 ms (170). If IMD 10 determines that the delay associated with the first probe pulse 110A is greater than the delay associated with the second probe pulse 110B, IMD 10 does not adjust the probe pulse intervals or the ESI (172).

Figure 9:
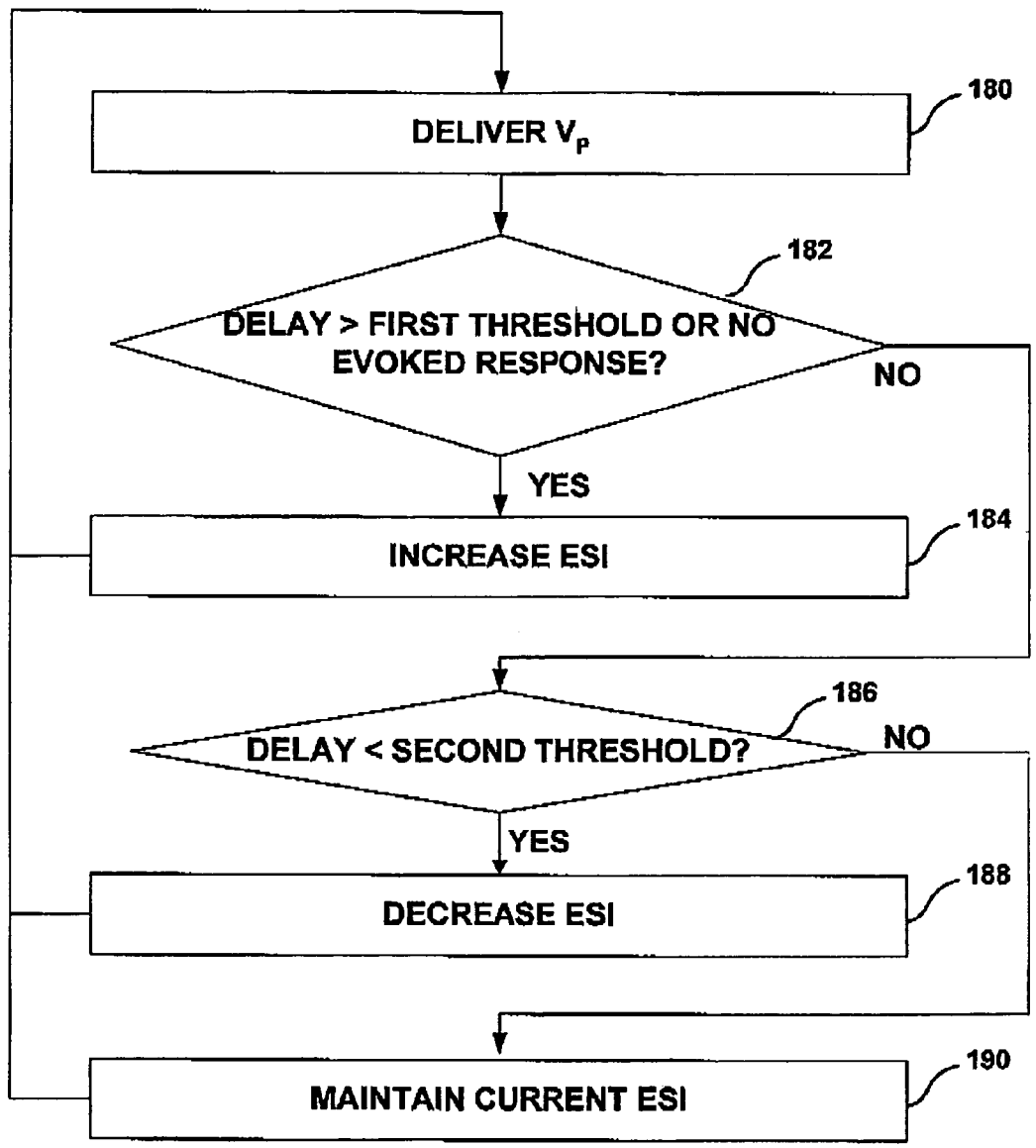
FIG. 9 is a flow diagram illustrating another example mode of operation of the implantable medical device of FIG. 1 to adjust the extra-systolic interval based on delays between delivery of extra-systolic stimulation pulses and resulting evoked responses.

FIG. 9 is a flow diagram illustrating another example mode of operation of IMD 10 to adjust the ESI based on delays between delivery of extra-systolic stimulation pulses and resulting evoked responses. Specifically, FIG. 9 illustrates a method in which IMD 10 periodically delivers probe pulses 110 a single, adjustable probe pulse delivery interval after detection of systolic depolarizations, and determines whether to adjust the ESI and the probe pulse delivery interval based on comparison of the delays between the probe pulses 110 and the evoked responses resulting from delivery of the probe pulses 110 with threshold values. By comparing the delay to the threshold values, IMD 10 is able to maintain the ESS therapy pulses on a desired portion of the latency curve and, hence, a desired distance from the boundary of the refractory period.

IMD 10 delivers a probe pulse 110 a probe pulse delivery period after detection of a systolic depolarization (180) and measures the delay between delivery of the probe pulse 110 and a resulting evoked response. If IMD 10 does not detect an evoked response resulting from delivery of the probe pulse 110, or determines the delay is greater than a first threshold (182), IMD 10 increases the probe pulse delivery interval and the ESI (184). If IMD 10 determines that the delay is less than a second threshold (186), IMD 10 decreases the probe pulse delivery interval and the ESI (188). If IMD 10 measures a delay that is between the thresholds, IMD does not change the probe pulse delivery interval or the ESI (190).

Figure 10:
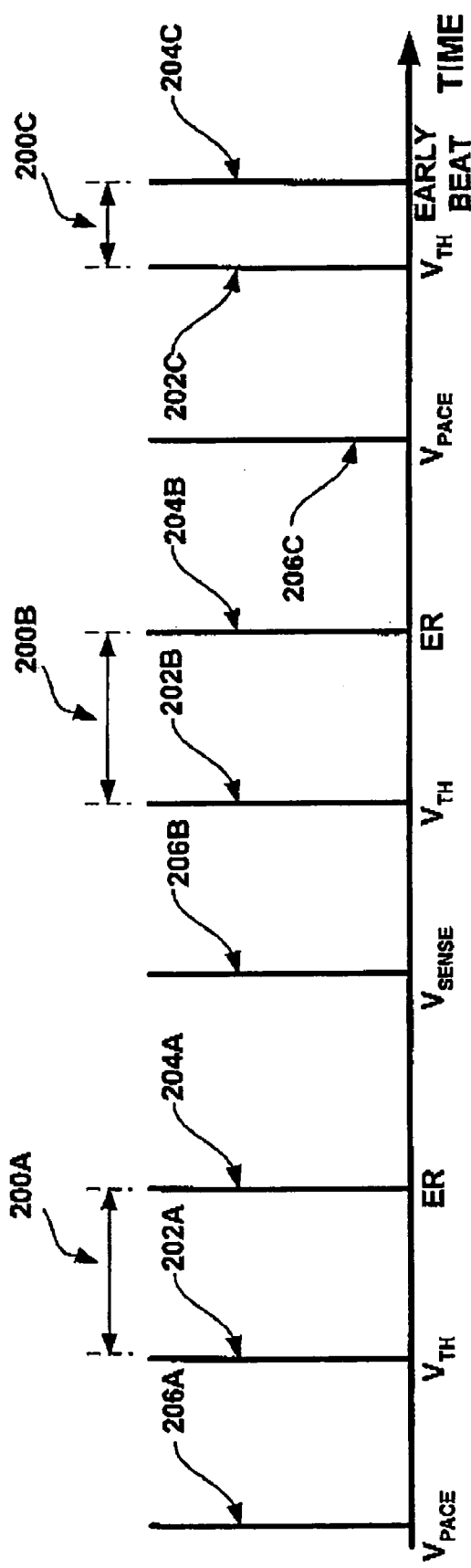
FIG. 10 is a timing diagram illustrating an example mode of operation of the implantable medical device of FIG. 1 to detect an arrhythmia of the heart based on delays between delivery of extra-systolic stimulation pulses and subsequent depolarizations.

FIG. 10 is a timing diagram illustrating an example mode of operation of IMD 10 to detect an arrhythmia of heart 16 based on delays 200 between delivery of extra-systolic stimulation pulses 202 and subsequent depolarizations 204. IMD 10 delivers ESS therapy pulses 202 after latency break point 152 (FIG. 7), and, consequently, the delays 200 between ESS therapy pulses 202 and the evoked responses 204A and 204B resulting from delivery of ESS therapy pulses will generally be stable. IMD 10 detects an arrhythmia of heart 16 by detecting instability of the lengths of delays 200.

In some embodiments, if IMD 10 determines that the difference between a current delay 200C and a previous delay 200B is greater than a threshold value, e.g., the current depolarization 204C occurs earlier than expected, IMD 10 treats the determination as a detection of an arrhythmia or takes action to determine if the early depolarization 204C is the result of an arrhythmia. In some embodiments, IMD 10 compares delays resulting from coupled pulses, e.g., ESS therapy pulses delivered after an intrinsic systolic depolarization such as ESS therapy pulse 202B delivered after intrinsic depolarization 206B, with previous delays resulting from coupled pulses, and compares delays resulting from paired pulses, e.g., ESS therapy pulses 202A and 202C delivered after a paced systolic depolarizations 206A and 206B, with previous delays resulting from paired pulses.

In some embodiments, IMD 10 suspends delivery of ESS therapy, e.g., for one cardiac cycle, in response to detection of early depolarization 204C. IMD 10 can more easily apply known arrhythmia detection algorithms while delivery of ESS therapy is suspended due to the absence of blanking intervals associated with delivery of ESS therapy pulses 202. In some embodiments, IMD 10 morphologically analyzes early depolarization 204C to determine whether depolarization 204C is the result of an arrhythmia. In some embodiments where IMD 10 delivers probe pulses to determine adjustments to the ESI of ESS therapy pulses as described above, IMD 10 does not measure the delay during cardiac cycles during which a probe pulse is delivered.

Figure 11:
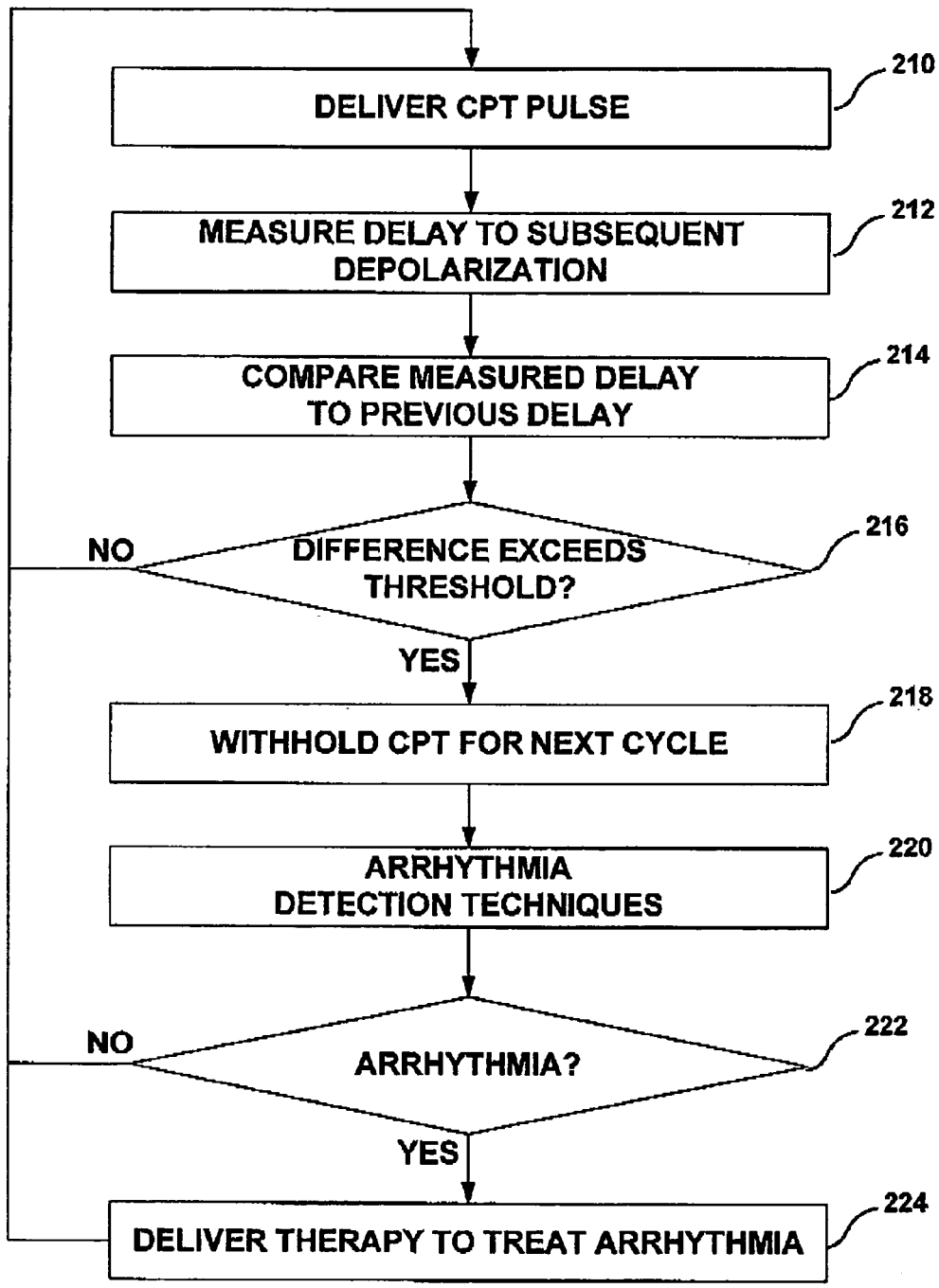
FIG. 11 is a flow diagram further illustrating the example mode of operation of FIG. 10.

FIG. 11 is a flow diagram further illustrating the example mode of operation of FIG. 10. IMD 10 delivers a ESS therapy pulse 202 (210) and measures a delay 200 between ESS therapy pulse 202 and a subsequently detected depolarization 204 (212). IMD 10 compares delay 200 to a previously measured delay 200 (214), and in some embodiments selects previously measured delay 200 based on whether the current and previous ESS therapy pulses 202 are both paired or coupled.

If IMD 10 determines that the difference between current and previous ESS therapy pulses 202 exceeds a threshold value (216), IMD 10 withholds delivery of a ESS therapy pulse 202 for the next cycle (218). During that cycle, IMD 10 applies arrhythmia detection techniques (220), such as well-known arrhythmia detection algorithms and/or morphological analysis of the early subsequently detected depolarization 204. In some embodiments, IMD 10 determines whether an arrhythmia is occurring based on the detection techniques (222), and delivers one or more therapies, such as ATP, cardioversion and/or defibrillation therapies, in response to a determination that an arrhythmia is occurring.

Various embodiments of the invention have been described. These and other embodiments are within the scope of the following claims.

The invention claimed is:

1. A method comprising:
estimating a length of a refractory period of a heart; and
setting a parameter for delivery of extra-systolic stimulation to the heart based on the estimated length of the refractory period of the heart, wherein estimation the length of the refractory period comprises:
detecting a systolic depolarization of the heart;
delivering a probe pulse to the heart an interval after detection of the systolic depolarization that is less than an extra-systolic interval;
determining whether the probe pulse captured the heart; and estimating the length of the refractory period based on the determination,
wherein delivering a probe pulse comprises delivering a probe pulse every N cardiac cycles, N being an integer greater than one, the method further comprising delivering an extra systolic pulse at the expiration of the extra-systolic interval after detection of a systolic depolarization of the heart during cardiac cycles in which a probe pulse is not delivered.

2. The method of claim 1, wherein determining whether the probe pulse captured the heart comprises:
monitoring electrical activity within the heart; and
detecting whether delivery of the probe pulse resulted in an evoked response.

3. The method of claim 1, wherein determining whether the probe pulse captured the heart comprises:
monitoring an intracardiac pressure; and
determining whether the probe pulse captured the heart based on a rate of change of the intracardiac pressure subsequent to delivery of the probe pulse.

4. The method of claim 1, further comprising:
determining that the probe pulse captured the heart; and
decreasing the interval for delivery of a subsequent probe pulse.

5. The method of claim 4, further comprising:
determining that the subsequently delivered probe pulse captured the heart; and
delivering a probe pulse every cardiac cycle until one of the delivered probe pulses does not capture the heart in response to the determination, each probe pulse delivered an interval after detection of a systolic depolarization of the heart that is less than a previous probe pulse.

6. The method of claim 4, further comprising:
determining that the probe pulse did not capture the heart; and
increasing the interval for delivery of a subsequent probe pulse.

7. The method of claim 6, further comprising: determining that the subsequently delivered probe pulse did not capture the heart; and delivering a probe pulse every cardiac cycle until one of the delivered probe pulses captures the heart in response to the determination, each probe pulse delivered an interval after detection of a systolic depolarization of the heart that is greater than a previous probe pulse.

8. A method comprising:
estimating a length of a refractory period of a heart; and
setting a parameter for delivery of extra-systolic stimulation to the heart based on the estimated length of the refractory period of the heart, wherein estimating the length of the refractory period comprises:
detecting a systolic depolarization of the heart;
delivering a probe pulse to the heart an interval after detection of the systolic depolarization that is less than an extra-systolic interval;
determining whether the probe pulse captured the heart; and estimating the length of the refractory period based on the determination,
wherein delivering a probe pulse comprises:
delivering a first probe pulse a first interval after detection of a first systolic depolarization of a first cardiac cycle;
delivering a second probe pulse a second interval after detection of a second systolic depolarization of a second cardiac cycle; and
determining that the first probe pulse captured the heart and the second probe pulse did not capture the heart, and
wherein estimating the length of the refractory period comprises estimating the length of the refractory period as a value between the first and second intervals.

9. A medical device comprising:
electrodes; and
a processor for controlling delivery of extra-systolic stimulation to a heart of a patient via the electrodes as a function of a parameter, wherein the processor estimates a length of a refractory period of the heart, and sets a value for the parameter bases on the estimated length of the refractory period of the heart, wherein the processor detects a systolic depolarization of the heart via the electrodes, controls delivery of a probe pulse to the heart an interval after detection of the systolic depolarization that is less than an extra-systolic interval, determines whether the probe pulse captured the heart, and estimates the length of the refractory period based on the determination, wherein the processor controls delivery of a probe pulse every N cardiac cycles, N being an integer greater than one, and controls delivery of an extra-systolic pulse, wherein the extra-systolic pulse is delivered at the expiration of the extra-systolic interval after detection of a systolic depolarization of the heart during cardiac cycles in which a probe pulse is not delivered.

10. The medical device of claim 9, wherein the processor monitors electrical activity within the heart via the electrodes, determines whether delivery of the probe pulse resulted in an evoked response based on the electrical activity to determine whether the probe pulse captured the heart.

11. The medical device of claim 9, further comprising a pressure sensor, wherein the processor monitors an intracardiac pressure via the pressure sensor, and determines whether the probe pulse captured the heart based on a rate of change of the intracardiac pressure subsequent to delivery of the probe pulse.

12. The medical device of claim 9, wherein the processor controls delivery of a first probe pulse a first interval after detection of a first systolic depolarization of a first cardiac cycle and a second probe pulse a second interval after a second systolic depolarization of a second cardiac cycle, determines that the first probe pulse captured the heart and the second probe pulse did not capture the heart, and estimates the length of the refractory period as a value between the first and second intervals.

13. The medical device of claim 9, wherein the processor determines that the probe pulse captured the heart, and decreases the interval for delivery of a subsequent probe pulse.

14. The medical device of claim 13, wherein the processor determines that the subsequently delivered probe pulse captured the heart, and controls delivery of a probe pulse every cardiac cycle until one of the delivered probe pulses does not capture the heart in response to the determination, each probe pulse delivered an interval after detection of a systolic depolarization of the heart that is less than a previous probe pulse.

15. The medical device of claim 9, wherein the processor determines that the probe pulse did not capture the heart, and increases the interval for delivery of a subsequent probe pulse.

16. The medical device of claim 15, wherein the processor determines that the subsequently delivered probe pulse did not capture the heart, and controls delivery of a probe pulse every cardiac cycle until one of the delivered probe pulses captures the heart in response to the determination, each probe pulse delivered an interval after detection of a systolic depolarization of the heart that is greater than a previous probe pulse.

17. A computer-readable medium comprising instructions that cause a programmable processor to:
estimate a length of a refractory period of a heart; and
set a parameter for delivery of extra-systolic stimulation to the heart based on the estimated length of the refractory period of the heart, wherein the instructions the instructions that cause a programmable processor to estimate the length of the refractory period comprise instructions that cause a programmable processor to:
detect a systolic depolarization of the heart;
control delivery of a probe pulse to the heart an intervsal after detection of the systolic depolarization that is less than an extra-systolic interval;
determine whether the probe pulse captured the heart; and
estimate the length of the refractory period based on the determination, wherein the instructions that cause a programmable processor to control delivery of a probe pulses comprise instructions that cause a programmable processor to control delivery of a first probe pulse a first interval after detection of a first systolic depolarization of a first cardiac cycle and a second probe pulse a second interval after detection of a second systolic depolarization of a second cardiac cycle, the medium further comprising instructions that cause a programmable processor to determine that the first probe pulse captured the heart and the second probe pulse did not capture the heart, and wherein the instructions that cause a programmable processor to estimate the length of the refractory period comprise instructions that cause a programmable processor to estimate the length of the refractory period as a value between the first and second intervals.

18. The computer-readable medium of claim 17, further comprising instructions that cause a programmable processor to:
determine that the probe pulse captured the heart; and
decrease the interval for delivery of a subsequent probe pulse.

19. The computer-readable medium of claim 18, further comprising instructions that cause a programmable processor to:
determine that the subsequently delivered probe pulse captured the heart; and
control delivery of a probe pulse every cardiac cycle until one of the delivered probe pulses does not capture the heart in response to the determination, each probe pulse delivered an interval after detection of a systolic depolarization of the heart that is less than a previous probe pulse.

20. The computer-readable medium of claim 17, further comprising instructions that cause a programmable processor to:
determine that the probe pulse did not capture the heart; and increase the interval for delivery of a subsequent probe pulse.

21. The computer-readable medium of claim 20, further comprising instructions that cause a programmable processor to:
determine that the subsequently delivered probe pulse did not capture the heart; and
control delivery of a probe pulse every cardiac cycle until one of the delivered probe pulses captures the heart in response to the determination, each probe pulse delivered an interval after detection of a systolic depolarization of the heart that is greater than a previous probe pulse.

22. A method comprising:
measuring a delay between delivery of a pulse to a heart and detection of an evoked response resulting from delivery of the pulse; and
adjusting a parameter for delivery of extra-systolic stimulation to the heart based on the delay,
wherein adjusting a parameter comprises adjusting an extra-systolic interval, wherein the pulse is a probe pulse, and wherein the method further comprises:
  detecting a systolic depolarization of the heart; and
  delivering the probe pulse an interval after detection of the systolic depolarization, the interval less than the extra-systolic interval,
wherein adjusting the extra-systolic interval comprises:
  comparing the delay to a threshold value; and
  adjusting the extra-systolic interval based on the comparison.

23. A method comprising:
  measuring a delay between delivery of a pulse to a heart and detection of an evoked response resulting from delivery of the pulse; and
  adjusting a parameter for delivery of extra-systolic stimulation to the heart based on the delay,
  wherein adjusting a parameter comprises adjusting an extra-systolic interval,
  wherein the pulse is a probe pulse, and
wherein the method further comprises:
  detecting a systolic depolarization of the heart; and
  delivering the probe pulse an interval after detection of the systolic depolarization, the interval less than the extra-systolic interval,
wherein delivering the probe pulse comprises delivering a probe pulse every N cardiac cycles, N being an integer greater than one, the method further comprising delivering extra-systolic pulses the extra-systolic interval after detection of systolic depolarizations of the heart during cardiac cycles in which a probe pulse is not delivered.

24. A method comprising
  measuring a delay between delivery of a pulse to a heart and detection of an evoked response resulting from delivery of the pulse; and
  adjusting a parameter for delivery of extra-systolic stimulation to the heart based on the delay,
  wherein adjusting a parameter comprises adjusting an extra-systolic interval,
  wherein the pulse is a probe, and wherein the method further comprises:
  detecting a systolic depolarization of the heart; and
  delivering the probe pulse an interval after detection of the systolic depolarization, the interval less than the extra-systolic interval,
wherein delivering the probe pulse comprises:
  delivering a first probe pulse of a pair a first interval after detection of a systolic depolarization of a first cardiac cycle; and
  delivering a second probe pulse of the pair a second interval after detection of a systolic depolarization of a second cardiac cycle,
  wherein the second interval is greater than the first interval, and the first and second intervals are less than the extra-systolic interval,
  wherein measuring a delay between delivery of the probe pulse and detection of the evoked response comprises measuring a first delay subsequent to delivery of the first probe pulse and a second delay subsequent to delivery of the second probe pulse, and
wherein adjusting the extra-systolic interval comprises adjusting the extra-systolic interval based on the first and second delays.

25. The method of claim 24, wherein adjusting the extra-systolic interval comprises:
  determining that the second delay is longer than the first delay; and
  increasing the extra-systolic interval in response to the determination.

26. The method of claim 24, wherein adjusting the extra-systolic interval comprises:
  determining that the first and second delays are substantially equal; and decreasing the extra-systolic interval in response to the determination.

27. The method of claim 24, wherein adjusting the extra-systolic interval comprises:
  determining that the first delay is greater than the second delay; and maintaining the extra-systolic interval at a current value in response to the determination.

28. A medical device comprising:
  electrodes; and
  a processor for controlling delivery of pulse and extra-systolic stimulation to a heart of a patient and detect evoked responses via the electrodes, wherein the processor measures a delay between delivery of a pulse to the heart and detection of an evoked response resulting from delivery of the pulse, and adjusts a parameter for delivery of extra-systolic stimulation to the heart based on the delay,
  wherein the parameter comprises and extra-systolic interval,
  wherein the pulse is a probe pulse, and the processor detects a systolic depolarization of the heart via the electrodes and controls delivery of the probe pulse to the heart an interval after detection of the systolic depolarization, the interval less than the extra-systolic interval,
wherein the processor compares the delay to a threshold value, and adjusts the extra-systolic interval based on the comparison.

29. A medical device comprising:
  electrodes; and
  a processor for controlling delivery of pulses and extra-systolic stimulation to a heart of a patient and detect evoked responses via the electrodes, wherein the processor measures a delay between delivery of a pulse to the heart and detection of an evoked response resulting from delivery of the pulse, and adjusts a parameter for delivery of extra-systolic stimulation to the heart on the delay,
  wherein the parameter comprises an extra-systolic interval,
  wherein the pulse is a probe pulse, and the processor detects a systolic depolarization of the heart via the electrodes and controls delivery of the probe pulse to the heart an interval after detection of the systolic depolarization, the interval less than the extra-systolic interval,
wherein the processor controls delivery of a probe pulse every N cardiac cycles, N being an integer greater than one, and controls delivery of extra-systolic, pulses wherein the extra-systolic pulse is delivered at the expiration of the extra-systolic interval after detection of systolic depolarizations during cardiac cycles in which a probe pulse is not delivered.

30. The medical device of claim 29, wherein the medical device is implantable within the patient.

31. The medical device of claim 29, wherein the medical device is a pacemaker.

32. A medical device comprising:
  electrodes; and
  a processor for controlling delivery of pulses and extra-systolic stimulation to a heart of a patient and detect evoked responses via the electrodes, wherein the processor measures a delay between delivery of a pulse to the heart and detection of an evoked response resulting from delivery of the pulse, and adjusts a parameter for delivery of extra-systolic stimulation to the heart based on the delay, wherein the parameter comprises an extra-systolic interval, wherein the pulse is a probe pulse, and the processor detects a systolic depolarization of the heat via the electrodes and controls delivery of the probe pulse to the heart an interval after detection of the systolic depolarization, the interval less than the extra-systolic interval, wherein the processor controls delivery of a first probe pulse of a pair a first interval after detection of a systolic depolarization of a first cardiac cycle, and controls delivery of a second probe pulse of the pair a second interval after a systolic depolarization of a second cardiac cycle, wherein the second interval is greater than the first interval, and the first and second intervals are less than the extra-systolic interval, and wherein the processor measures a first delay subsequent to delivery of the first probe pulse and a second delay subsequent to delivery of the second probe pulse, and adjusts the extra-systolic interval based on the first and second delays.

33. The medical device of claim 32, wherein the processor determines that the second delay is longer than the first delay, and increases the extra-systolic interval in response to the determination.

34. The medical device of claim 32, wherein the processor determines that the first and second delays are substantially equal, and decreases the extra-systolic interval in response to the determination.

35. The medical device of claim 32, wherein the processor determines that the first delay is greater than the second delay, and maintains the extra-systolic interval at a current value in response to the determination.

36. A computer-readable medium comprising instructions that cause a programmable processor to:
measure a delay between delivery of a pulse to a heart and detection of an evoked response resulting from delivery of the pulse; and
adjust a parameter for delivery of extra-systolic stimulation to heart bases on the delay,
wherein the pulse is a probe pulse, and wherein the medium further comprises instructions that cause a programmable processor to:
detect a systolic depolarization of the heart; and
control delivery of the probe pulse to the heart an interval after detection of the systolic depolarization, the interval less than the extra-systolic interval,
wherein the parameter comprises an extra-systolic interval, and
wherein the instructions that cause a programmable processor to control delivery of the probe pulse comprise instructions that cause a programmable processor to control delivery of a probe pulse every N cardiac cycles, N being an integer greater than one, the medium further comprising instructions that cause a programmable processor to control delivery of extrasystolic pulses at the expiration of the extra-systolic interval after detection of systolic depolarizations of the heart during cardiac cycles in which a probe pulse is not delivered.

37. The computer-readable medium of claim 36, wherein the instructions that cause a programmable processor to adjust the extra-systolic interval comprise instructions that cause a programmable processor to:
compare the delay to a threshold value; and
adjust the extra-systolic interval based on the comparison.

38. The computer-readable medium of claim 36, wherein the instructions that cause a programmable processor to control delivery of the probe pulse comprise instructions that cause a programmable processor to:
control delivery of a first probe pulse of a pair a first interval after detection of a systolic depolarization of a first cardiac cycle; and
control delivery of a second probe pulse of the pair a second interval after a systolic depolarization of a second cardiac cycle,
wherein the second interval is greater than the first interval, and the first and second intervals are less than the extra-systolic interval,
wherein the instructions that cause a programmable processor to measure a delay between delivery of the probe pulse and detection of the evoked response comprise instructions that cause a programmable processor to measure a first delay subsequent to delivery of the first probe pulse and a second delay subsequent to delivery of the second probe pulse, and
wherein the instructions that cause a programmable processor to adjust the extra-systolic interval comprise instructions that cause a programmable processor to adjust the extra-systolic interval based on the first and second delays.

39. The computer-readable medium of claim 38, wherein the instructions that cause a programmable processor to adjust the extra-systolic interval comprise instructions that cause a programmable processor to:
determine that the second delay is longer than the first delay; and
increase the extra-systolic interval in response to the determination.

40. The computer-readable medium of claim 38, wherein the instructions that cause a programmable processor to adjust the extra-systolic interval comprise instructions that cause a programmable processor to:
determine that the first and second delays are substantially equal; and
decrease the extra-systolic interval in response to the determination.

41. The computer-readable medium of claim 38, wherein the instructions that cause a programmable processor to adjust the extra-systolic interval comprise instructions that cause a programmable processor to:
determine that the first delay is greater than the second delay; and
maintain the extra-systolic interval at a current value in response to the determination.

* * * * *

UNITED STATES PATENT AND TRADEMARK OFFICE
CERTIFICATE OF CORRECTION

PATENT NO. : 7,184,832 B2 Page 1 of 1
APPLICATION NO. : 10/680528
DATED : February 27, 2007
INVENTOR(S) : Deno et al.

It is certified that error appears in the above-identified patent and that said Letters Patent is hereby corrected as shown below:

Column 16, line 64 please change "bases on" to --based on--.

Column 21, line 60 please change "extrasystolic" to --extra-systolic--.

Signed and Sealed this

Second Day of October, 2007

JON W. DUDAS
*Director of the United States Patent and Trademark Office*